(12) United States Patent
Cindrich et al.

(10) Patent No.: US 10,285,834 B2
(45) Date of Patent: May 14, 2019

(54) VASCULAR PROSTHESIS DEPLOYMENT DEVICE AND METHOD OF USE

(71) Applicant: Merit Medical Systems, Inc., South Jordan, UT (US)

(72) Inventors: Christopher Noel Cindrich, Draper, UT (US); John William Hall, North Salt Lake, UT (US); Zeke Eller, Plano, TX (US); Thomas Robinson, Addison, TX (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 5 days.

(21) Appl. No.: 15/061,107

(22) Filed: Mar. 4, 2016

(65) Prior Publication Data

US 2016/0256306 A1 Sep. 8, 2016

Related U.S. Application Data

(60) Provisional application No. 62/129,006, filed on Mar. 5, 2015.

(51) Int. Cl.
*A61F 2/95* (2013.01)
*A61F 2/844* (2013.01)
*A61F 2/966* (2013.01)

(52) U.S. Cl.
CPC .............. *A61F 2/966* (2013.01); *A61F 2/844* (2013.01); *A61F 2002/9517* (2013.01)

(58) Field of Classification Search
CPC .. A61F 2/966; A61F 2/962; A61F 2002/9517; A61F 2/844
See application file for complete search history.

(56) References Cited

U.S. PATENT DOCUMENTS

| | | | |
|---|---|---|---|
| 5,201,757 | A | 4/1993 | Heyn et al. |
| 5,591,172 | A | 1/1997 | Bachmann et al. |
| 5,591,196 | A | 1/1997 | Marin et al. |
| 5,733,325 | A | 3/1998 | Robinson et al. |
| 5,755,769 | A | 5/1998 | Richard et al. |
| 5,759,186 | A | 6/1998 | Bachmann et al. |
| 5,824,041 | A | 10/1998 | Lenker et al. |

(Continued)

FOREIGN PATENT DOCUMENTS

| | | |
|---|---|---|
| DE | 9209908 | 9/1992 |
| DE | 4323866 | 1/1994 |

(Continued)

OTHER PUBLICATIONS

International Search Report and Written Opinion dated Jun. 22, 2016 for PCT/US2016/020900.

(Continued)

*Primary Examiner* — Katrina M Stransky
(74) *Attorney, Agent, or Firm* — Stoel Rives LLP

(57) ABSTRACT

A vascular prosthesis deployment device and related methods are disclosed. In some embodiments the deployment device may provide audible, tactile, or visual feedback to a practitioner as to the degree of deployment of a prosthesis. The deployment device may also provide mechanical advantage when deploying a prosthesis. The deployment device may be configured to incrementally deploy a prosthesis.

18 Claims, 10 Drawing Sheets

(56) References Cited

U.S. PATENT DOCUMENTS

| | | |
|---|---|---|
| 5,868,755 A | 2/1999 | Kanner et al. |
| 5,876,448 A | 3/1999 | Thompson et al. |
| 5,916,147 A | 6/1999 | Boury |
| 5,968,052 A * | 10/1999 | Sullivan, III ............ A61F 2/95 606/206 |
| 6,093,194 A | 7/2000 | Mikus et al. |
| 6,123,715 A | 9/2000 | Amplatz |
| 6,143,021 A | 11/2000 | Staehle |
| 6,146,415 A | 11/2000 | Fitz |
| 6,162,231 A | 12/2000 | Mikus et al. |
| 6,241,757 B1 | 6/2001 | An et al. |
| 6,283,992 B1 | 9/2001 | Hankh et al. |
| 6,368,339 B1 | 4/2002 | Amplatz |
| 6,383,211 B1 | 5/2002 | Staehle |
| 6,391,051 B2 | 5/2002 | Sullivan, III et al. |
| 6,413,269 B1 | 7/2002 | Bui et al. |
| 6,416,545 B1 | 7/2002 | Mikus et al. |
| 6,428,566 B1 | 8/2002 | Holt |
| 6,447,531 B1 | 9/2002 | Amplatz |
| 6,514,261 B1 | 2/2003 | Randall et al. |
| 6,530,933 B1 | 3/2003 | Yeung et al. |
| 6,599,296 B1 | 7/2003 | Gillick et al. |
| 6,599,308 B2 | 7/2003 | Amplatz |
| 6,616,675 B1 | 9/2003 | Evard et al. |
| 6,629,981 B2 | 10/2003 | Dennis et al. |
| 6,645,143 B2 | 11/2003 | Vantassel et al. |
| 6,669,719 B2 | 12/2003 | Wallace et al. |
| 6,726,712 B1 | 4/2004 | Raeder-Devens et al. |
| 6,746,480 B2 | 6/2004 | Scholz et al. |
| 6,770,101 B2 | 8/2004 | Desmond, III et al. |
| 6,776,791 B1 | 8/2004 | Jody et al. |
| 6,821,295 B1 | 11/2004 | Farrar |
| 6,866,669 B2 | 3/2005 | Buzzard et al. |
| 6,893,413 B2 | 5/2005 | Martin |
| 6,926,732 B2 | 8/2005 | Derus et al. |
| 6,955,685 B2 | 10/2005 | Escamilla et al. |
| 7,004,966 B2 | 2/2006 | Edwin et al. |
| 7,083,640 B2 | 8/2006 | Lombardi et al. |
| 7,309,350 B2 | 12/2007 | Landreville et al. |
| 7,309,351 B2 | 12/2007 | Escamilla et al. |
| 7,393,357 B2 | 7/2008 | Stelter et al. |
| 7,591,848 B2 | 9/2009 | Allen |
| 7,637,942 B2 | 12/2009 | Mangiardi et al. |
| 7,731,654 B2 | 6/2010 | Mangiardi et al. |
| 7,959,671 B2 | 6/2011 | Mangiardi et al. |
| 8,012,194 B2 | 9/2011 | Edwin et al. |
| 8,206,436 B2 | 6/2012 | Mangiardi et al. |
| 8,262,719 B2 | 9/2012 | Erickson et al. |
| 8,357,193 B2 | 1/2013 | Phan et al. |
| 8,414,635 B2 | 4/2013 | Hyodoh et al. |
| 8,425,539 B2 | 4/2013 | Binmoeller et al. |
| 8,439,934 B2 | 5/2013 | Satasiya et al. |
| 8,454,623 B2 | 6/2013 | Binmoeller et al. |
| 8,454,632 B2 | 6/2013 | Binmoeller et al. |
| 8,518,099 B2 | 8/2013 | Chanduszko et al. |
| 8,524,132 B2 | 9/2013 | Von Oepen et al. |
| 8,535,366 B2 | 9/2013 | Mangiardi et al. |
| 8,652,099 B2 | 2/2014 | Fierens et al. |
| 8,677,874 B2 | 3/2014 | Lilburn et al. |
| 8,696,611 B2 | 4/2014 | Yaacov et al. |
| 8,715,334 B2 | 5/2014 | Clerc et al. |
| 8,906,081 B2 | 12/2014 | Cully et al. |
| 8,926,683 B2 | 1/2015 | Darla et al. |
| 9,155,643 B2 | 10/2015 | Clerc et al. |
| 9,192,496 B2 | 11/2015 | Robinson |
| 9,259,336 B2 | 2/2016 | Schaeffer et al. |
| 9,284,637 B2 | 3/2016 | Boyle et al. |
| 9,381,041 B2 | 7/2016 | Brown et al. |
| 2001/0037141 A1 | 11/2001 | Yee et al. |
| 2002/0138095 A1 | 9/2002 | Mazzocchi et al. |
| 2002/0151967 A1 | 10/2002 | Mikus et al. |
| 2002/0183827 A1 | 12/2002 | Derus et al. |
| 2002/0193749 A1 | 12/2002 | Olovson |
| 2003/0028236 A1 | 2/2003 | Gillick |
| 2003/0050686 A1 | 3/2003 | Raeder-Devens et al. |
| 2003/0135265 A1 | 7/2003 | Stinson |
| 2003/0135268 A1 | 7/2003 | Desai |
| 2003/0167060 A1 | 9/2003 | Buzzard et al. |
| 2004/0030381 A1 | 2/2004 | Shu |
| 2004/0193243 A1 | 9/2004 | Mangiardi et al. |
| 2004/0267281 A1 | 12/2004 | Harari et al. |
| 2005/0090887 A1 | 4/2005 | Pryor |
| 2005/0125050 A1 | 6/2005 | Carter et al. |
| 2005/0149160 A1 | 7/2005 | McFerran |
| 2005/0278010 A1 | 12/2005 | Richardson |
| 2006/0155368 A1 | 7/2006 | Shin |
| 2006/0258972 A1 | 11/2006 | Mangiardi et al. |
| 2007/0005122 A1 | 1/2007 | Inoug |
| 2007/0043421 A1 | 2/2007 | Mangiardi et al. |
| 2007/0100421 A1 | 5/2007 | Griffin |
| 2007/0156225 A1 | 7/2007 | George et al. |
| 2007/0179590 A1 | 8/2007 | Lu et al. |
| 2007/0208350 A1 | 9/2007 | Gunderson |
| 2007/0250150 A1 | 10/2007 | Pal et al. |
| 2007/0270932 A1 | 11/2007 | Headley et al. |
| 2008/0114443 A1 | 5/2008 | Mitchell et al. |
| 2008/0228256 A1 | 9/2008 | Erickson et al. |
| 2008/0288042 A1 | 11/2008 | Purdy et al. |
| 2009/0099636 A1 | 4/2009 | Chanduszko et al. |
| 2009/0099647 A1 | 4/2009 | Glimsdale et al. |
| 2009/0118740 A1 | 5/2009 | Mangiardi et al. |
| 2009/0157158 A1 | 6/2009 | Ondracek |
| 2009/0187240 A1 | 7/2009 | Clerc |
| 2009/0192518 A1 | 7/2009 | Golden et al. |
| 2009/0292262 A1 | 11/2009 | Adams et al. |
| 2010/0023032 A1 | 1/2010 | Granja et al. |
| 2010/0023132 A1 | 1/2010 | Imran |
| 2010/0030256 A1 | 2/2010 | Dubrul et al. |
| 2010/0049295 A1 | 2/2010 | Satasiya et al. |
| 2010/0057145 A1 | 3/2010 | Bhatnagar et al. |
| 2010/0057185 A1 | 3/2010 | Melsheimer et al. |
| 2010/0145431 A1 | 6/2010 | Wu et al. |
| 2010/0252470 A1 | 10/2010 | Ryan et al. |
| 2011/0015616 A1 | 1/2011 | Straubinger et al. |
| 2011/0082464 A1 | 4/2011 | Douk et al. |
| 2011/0190862 A1 | 8/2011 | Mehran et al. |
| 2011/0208296 A1 | 8/2011 | Duffy et al. |
| 2011/0264191 A1 | 10/2011 | Rothstein |
| 2011/0288482 A1 | 11/2011 | Farrell et al. |
| 2011/0307070 A1 | 12/2011 | Clerc et al. |
| 2011/0319980 A1 | 12/2011 | Ryan |
| 2012/0046729 A1 | 2/2012 | Von Oepen et al. |
| 2012/0136426 A1 | 5/2012 | Phan et al. |
| 2012/0296257 A1 | 11/2012 | Van Dan et al. |
| 2012/0303112 A1 | 11/2012 | Armstrong et al. |
| 2012/0310320 A1 | 12/2012 | Gill et al. |
| 2013/0018215 A1 | 1/2013 | Snider et al. |
| 2013/0110221 A1 | 5/2013 | Campbell et al. |
| 2013/0116770 A1 | 5/2013 | Robinson |
| 2013/0116771 A1 | 5/2013 | Robinson |
| 2013/0116772 A1 | 5/2013 | Robinson et al. |
| 2013/0158673 A1 | 6/2013 | Toomey |
| 2013/0184833 A1 | 7/2013 | Ryan et al. |
| 2013/0197623 A1 | 8/2013 | McHugo |
| 2013/0231689 A1 | 9/2013 | Binmoeller et al. |
| 2013/0253546 A1 | 9/2013 | Sander et al. |
| 2013/0274870 A1 | 10/2013 | Lombardi et al. |
| 2014/0074065 A1 | 3/2014 | Muni et al. |
| 2014/0074219 A1 | 3/2014 | Hingston et al. |
| 2014/0236064 A1 | 8/2014 | Binmoeller et al. |
| 2014/0243992 A1 | 9/2014 | Walsh et al. |
| 2014/0288636 A1 | 9/2014 | Headley, Jr. et al. |
| 2014/0303709 A1 | 10/2014 | Dwork |
| 2014/0330305 A1 | 11/2014 | Rood et al. |
| 2014/0350694 A1 | 11/2014 | Behan |
| 2014/0364959 A1 | 12/2014 | Attar et al. |
| 2015/0100133 A1 | 4/2015 | Xie et al. |
| 2015/0112377 A1 | 4/2015 | Arnone et al. |
| 2015/0173919 A1 | 6/2015 | Baldwin |
| 2015/0313595 A1 | 11/2015 | Houshton et al. |
| 2015/0313599 A1 | 11/2015 | Johnson et al. |
| 2016/0081823 A1 | 3/2016 | Majercak |
| 2016/0081832 A1 | 3/2016 | Hingston et al. |

(56) References Cited

U.S. PATENT DOCUMENTS

| | | | |
|---|---|---|---|
| 2016/0120678 A1* | 5/2016 | Green | A61F 2/966 623/1.11 |
| 2016/0242846 A1 | 8/2016 | Brown et al. | |
| 2017/0035424 A1 | 2/2017 | Binmoeller et al. | |
| 2017/0035426 A1 | 2/2017 | Phan et al. | |
| 2017/0035427 A1 | 2/2017 | Sander et al. | |
| 2017/0035428 A1 | 2/2017 | Binmoeller et al. | |

FOREIGN PATENT DOCUMENTS

| | | |
|---|---|---|
| DE | 102005051469 | 4/2007 |
| EP | 0364420 | 4/1990 |
| EP | 0872220 | 10/1998 |
| EP | 1637092 | 3/2006 |
| EP | 2522316 | 11/2012 |
| WO | 199631174 | 10/1996 |
| WO | 2000078246 | 12/2000 |
| WO | 2002087470 | 11/2002 |
| WO | 2003090644 | 11/2003 |
| WO | 2004030571 | 4/2004 |
| WO | 2005070095 | 8/2005 |
| WO | 2008042266 | 4/2008 |
| WO | 2010130297 | 11/2010 |
| WO | 2012062603 | 10/2012 |
| WO | 2013045262 | 4/2013 |
| WO | 2013066883 | 10/2013 |

OTHER PUBLICATIONS

European Examination Report dated Feb. 18, 2015 for EP09791142.4.
European Search Report dated Feb. 3, 2015 for EP12846255.3.
European Search Report dated May 4, 2007 for EP05705271.4.
European Search Report dated Jun. 30, 2017 for EP11846358.7.
International Preliminary Report dated May 15, 2014 for PCT/US2012/062603.
International Publication and Search Report dated Jun. 14, 2012 for WO2012078794.
International Publication and Search Report dated Feb. 25, 2012 for WO2010021836.
International Publication and Search Report dated Aug. 4, 2005 for WO2005070095.
International Search Report and Written Opinion dated Mar. 16, 2012 for PCT/US2011/063799.
International Search Report and Written Opinion dated Mar. 29, 2013 for PCT/US2012/062603.
International Search Report and Written Opinion dated Sep. 28, 2005 for PCT/US2005/000515.
International Search Report and Written Opinion dated Oct. 29, 2009 for PCT/US2009/052691.
International Search Report and Written Opinion dated Nov. 23, 2006 for PCT/US2006/018811.
Notice of Allowance dated Jan. 14, 2015 for U.S. Appl. No. 11/432,964.
Notice of Allowance dated Mar. 6, 2013 for U.S. Appl. No. 12/535,980.
Notice of Allowance dated Jun. 11, 2013 for U.S. Appl. No. 10/585,430.
Notice of Allowance dated Jun. 22, 2016 for U.S. Appl. No. 13/664,267.
Notice of Allowance dated Aug. 12, 2015 for U.S. Appl. No. 13/664,200.
Notice of Allowance dated Sep. 23, 2016 for U.S. Appl. No. 13/664,234.
Notice of Allowance dated Oct. 21, 2014 for U.S. Appl. No. 13/313,929.
Office Action dated Jan. 3, 2014 for U.S. Appl. No. 11/432,964.
Office Action dated Jan. 22, 2013 for U.S. Appl. No. 10/585,430.
Office Action dated Jan. 31, 2012 for U.S. Appl. No. 10/585,430.
Office Action dated Mar. 16, 2015 for U.S. Appl. No. 13/664,234.
Office Action dated Mar. 22, 2016 for U.S. Appl. No. 13/664,234.
Office Action dated Mar. 24, 2015 for U.S. Appl. No. 13/664,267.
Office Action dated Apr. 6, 2016 for U.S. Appl. No. 13/664,137.
Office Action dated May 5, 2014 for U.S. Appl. No. 13/313,929.
Office Action dated May 25, 2012 for U.S. Appl. No. 12/535,980.
Office Action dated Jun. 7, 2011 for U.S. Appl. No. 10/585,430.
Office Action dated Jul. 9, 2009 for U.S. Appl. No. 11/432,964.
Office Action dated Jul. 25, 2013 for U.S. Appl. No. 11/432,964.
Office Action dated Aug. 13, 2012 for U.S. Appl. No. 10/585,430.
Office Action dated Oct. 7, 2015 for U.S. Appl. No. 13/664,234.
Office Action dated Oct. 16, 2015 for U.S. Appl. No. 13/664,267.
Office Action dated Nov. 9, 2010 for U.S. Appl. No. 10/585,430.
Office Action dated Nov. 14, 2012 for U.S. Appl. No. 12/535,980.
Office Action dated Nov. 19, 2015 for U.S. Appl. No. 13/664,137.
Office Action dated Nov. 30, 2016 for U.S. Appl. No. 13/664,137.
Office Action dated Dec. 7, 2009 for U.S. Appl. No. 11/432,964.
Office Action dated Dec. 8, 2009 for U.S. Appl. No. 10/585,430.
Supplementary European Search Report dated May 4, 2007 for EP05705271.4.
Sen, et al., Laplace's Equation for Convective Scalar Transport in Potential Flow, Proc. R. Soc. Lond. A 456, pp. 3041-3045 ,2000.
International Search Report and Written Opinion dated Jun. 29, 2018 for PCT/US2018/022340.
International Search Report and Written Opinion dated Jun. 29, 2018 for PCT/US2018/022344.
Kawakami, et al.,Endoscopic Ultrasound-Guided Transluminal Drainage for Peripancreatic Fluid Collections: Where are we now?, Gut and Liver, vol. 8 No. 4 ,2014 ,341-355.
Sizarov, et al.,Novel materials and Devices in the Transcatheter Creation of vascular Anastomosis—The Future Comes Slowly (Part 2), Archives of Cardiovascular Diseases, vol. 109 No. 4, 2016, 286-295.
Weilert, et al.,Specially Designed Stents for Translumenal Drainage, Gastrointestinal Intervention, vol. 4 No. 1 ,2015 ,40-45.
Notice of Allowance dated Sep. 6, 2018 for U.S. Appl. No. 29/597,873.
European Search Reported dated Sep. 24, 2018 for EP16759580.

* cited by examiner

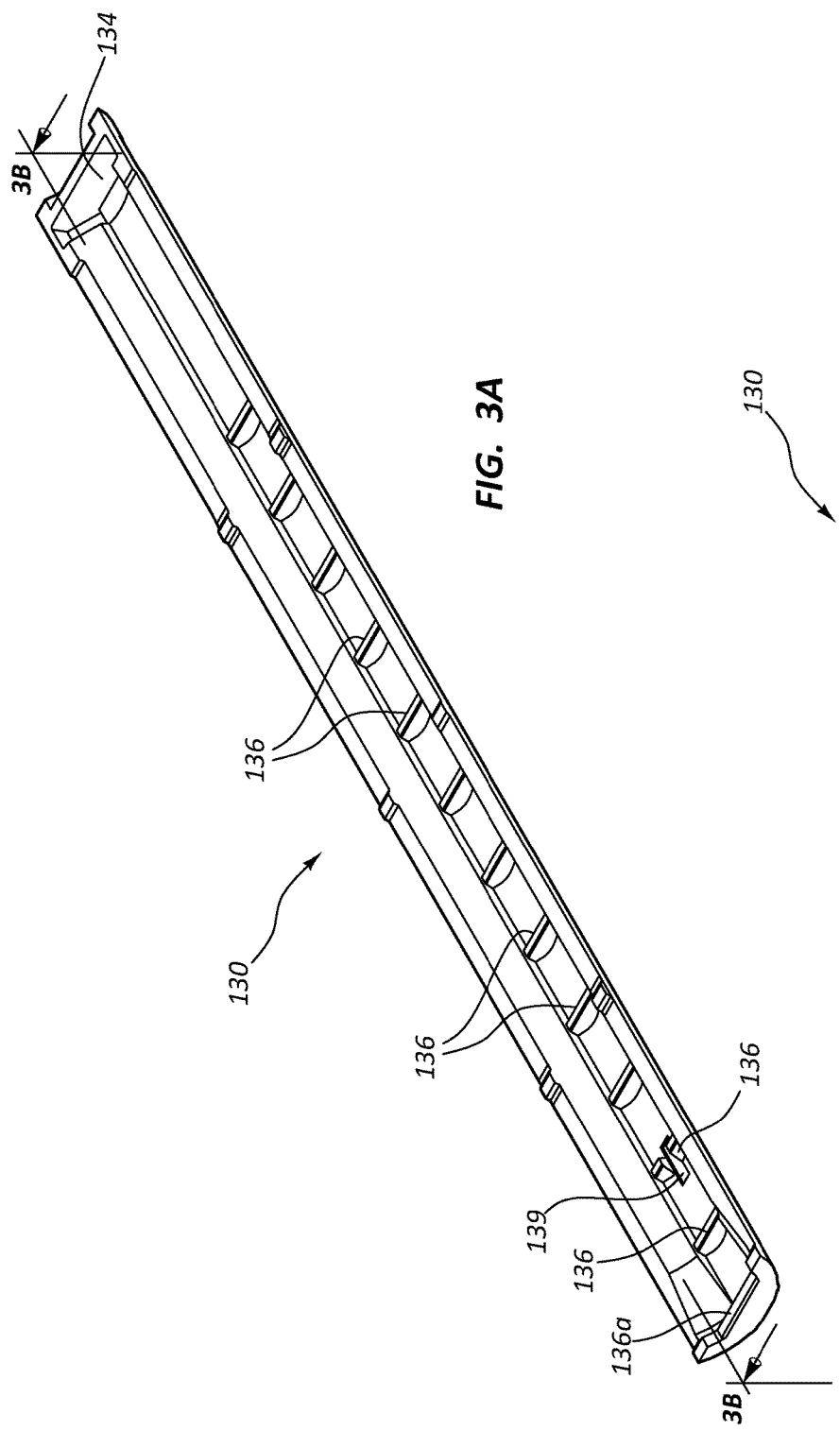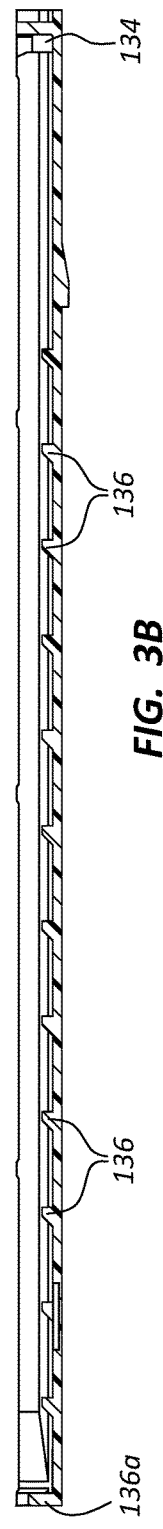

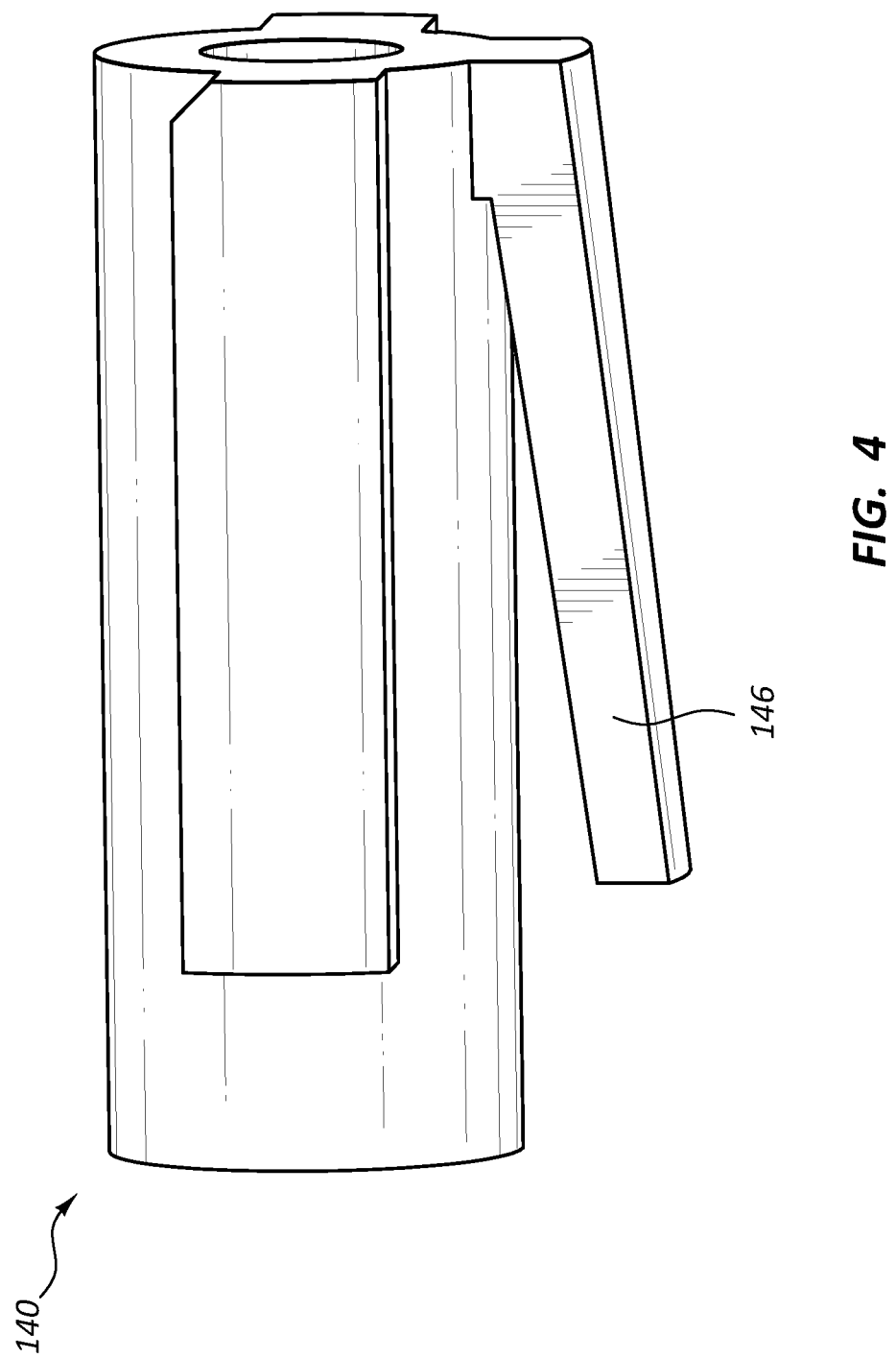

VASCULAR PROSTHESIS DEPLOYMENT DEVICE AND METHOD OF USE

RELATED APPLICATIONS

This application claims priority to U.S. Provisional Application No. 62/129,006, filed on Mar. 5, 2015 and titled, "Vascular Prosthesis Deployment Device and Method of Use," which is hereby incorporated by reference in its entirety.

TECHNICAL FIELD

The present disclosure relates generally to medical devices. More specifically, the present disclosure relates vascular prosthesis deployment devices, including deployment devices for self-expanding vascular prosthesis such as stents and stent-grafts.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 3A is a perspective view of a ratchet slide component of the deployment device of FIGS. 1 and 2.

FIG. 3B is a cross-sectional view of the ratchet slide of FIG. 3A.

FIG. 4 is a side view of a carrier component of the deployment device of FIGS. 1 and 2.

DETAILED DESCRIPTION

Figure 1:
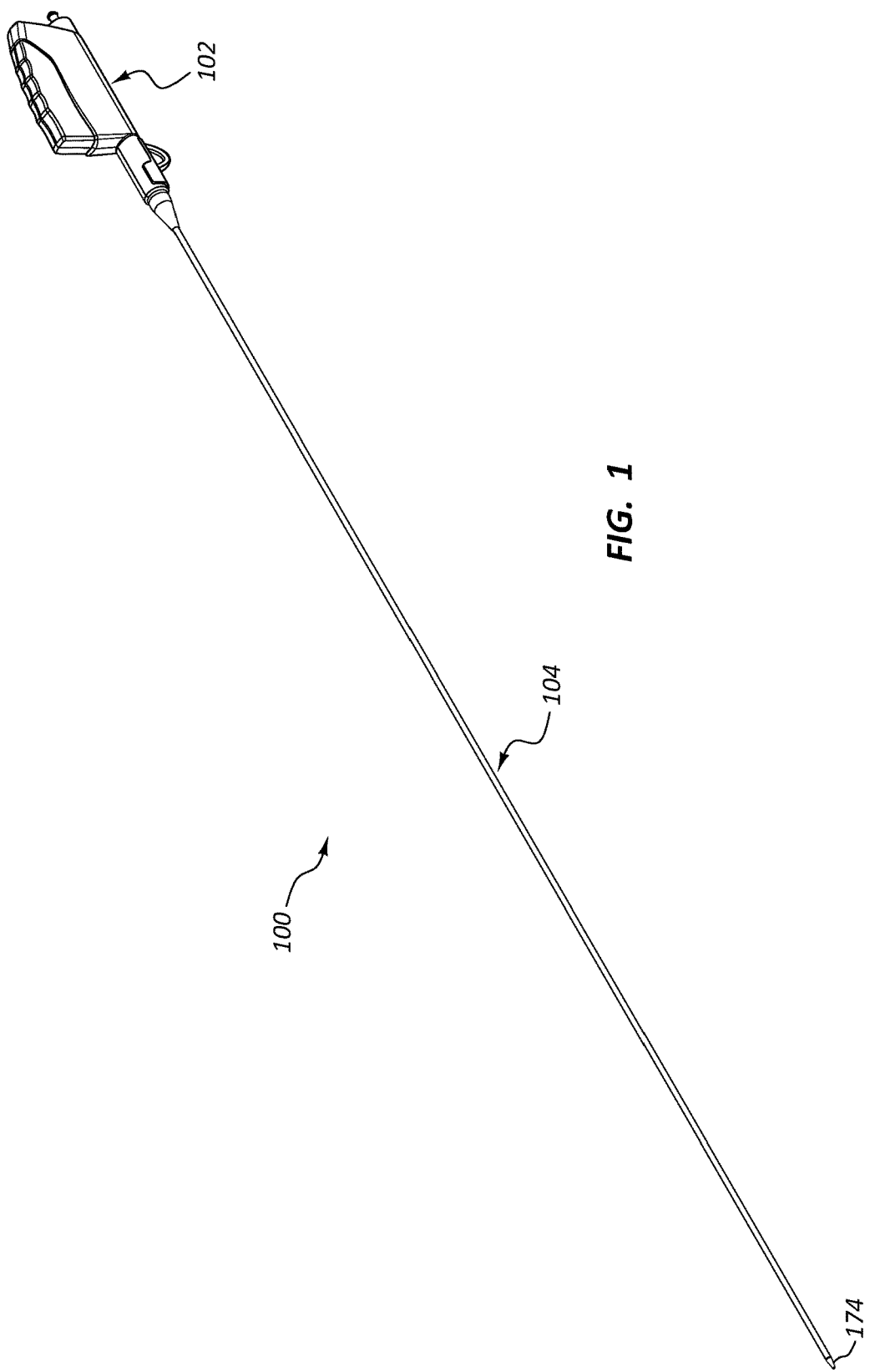
FIG. 1 is a perspective view of a deployment device.

Deployment devices may be configured to deliver a medical appliance to a location within a patient's body and deploy the medical appliance within the patient's body. Though specific examples recited herein may refer to deployment of devices within the vasculature, analogous concepts and devices may be used in various other locations within the body, including for placement and deployment of medical appliances in the gastrointestinal tract (including, for example, within the esophagus, intestines, stomach, small bowel, colon, and biliary duct); the respiratory system (including, for example, within the trachea, bronchial tubes, lungs, nasal passages, and sinuses); or any other location within the body, both within bodily lumens (for example, the ureter, the urethra, and/or any of the lumens discussed above) and within other bodily structures.

Furthermore, though specific examples herein may refer to deployment of vascular prosthesis such as stents, deployment of a wide variety of medical appliances are within the scope of this disclosure, including, stents, stent-grafts, shunts, grafts, and so forth. Additionally, the deployment device disclosed herein may be configured to deliver and deploy self-expanding medical appliances, including stents configured to expand within a bodily lumen upon deployment.

As used herein, delivery of a medical appliance generally refers to placement of a medical appliance in the body, including displacement of the appliance along a bodily lumen to a treatment site. For example, delivery includes displacement of a crimped stent along a vascular lumen from an insertion site to a treatment location. Deployment of a medical appliance refers to placement of the medical appliance within the body such that the medical appliance interacts with the body at the point of treatment. For example, deployment includes releasing a crimped or otherwise constrained self-expanding stent from a deployment device such that the stent expands and contacts a lumen of the vasculature.

Deployment devices within the scope of this disclosure may be configured to incrementally deploy a medical appliance. Incremental deployment may facilitate desired placement of the medical appliance due to the degree of control afforded a practitioner during deployment. A practitioner may, for example, desire to deploy a portion of a stent, make adjustments to placement within the vasculature or confirm the location of the stent, prior to deploying the remaining portion of the stent. Such processes may be iterative, with a practitioner deploying a portion of a stent, confirming placement, deploying an additional portion, again confirming placement, and so forth until the stent is fully deployed.

Deployment devices within the scope of this disclosure may be configured to provided visual, audible, tactile, or other feedback relating to the degree to which a medical appliance has been deployed. Multiple types of feedback may enhance a practitioner's level of control over the procedure due to the multiple indications regarding location or degree of deployment of the medical appliance.

Moreover, deployment devices within the scope of this disclosure may provide a degree of mechanical advantage during deployment, for example, through use of levers to decrease the force used to deploy a device. Mechanical advantage may thus increase a user's comfort and level of control during use. Still further, deployment devices within the scope of this disclosure may be ergonomically designed, presenting an actuation input disposed such that a practitioner can directly engage and utilize the device, without reposition his or her hand or body. Deployment devices within the scope of this disclosure may also be configured for one handed actuation and may be configured for ambidextrous use.

It will be readily understood that the components of the embodiments as generally described and illustrated in the figures herein could be arranged and designed in a wide variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluidic, and thermal interaction. Two components may be coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Again, though the embodiments specifically described below may reference a stent deployment device specifically, the concepts, devices, and assemblies discussed below may be analogously applied to deployment of a wide variety of medical appliances in a wide variety of locations within the body.

FIG. 1 is a perspective view of a deployment device 100. The deployment device 100 comprises a handle assembly 102 adjacent the proximal end of the deployment device 100. An elongate delivery catheter assembly 104 extends distally from the handle assembly 102 to a delivery tip. The handle assembly 102 may provide a proximal user input, with one or more components configured to allow a practitioner to deploy or otherwise manipulate a stent disposed within the delivery catheter assembly 104.

In use, the handle assembly 102 may be disposed outside of a patient's body, while the delivery catheter assembly 104 is advanced to a treatment location within the patient's body. For example, the delivery catheter assembly 104 may be advanced from an insertion site (such as, for example, a femoral or jugular insertion site) to a treatment location within the vasculature. As further detailed below, the delivery catheter assembly 104 may be configured to be advanced through bends, turns, or other structures within the anatomy of the vasculature. Again, as detailed below, a stent may be disposed within a portion of the delivery catheter assembly 104 such that a practitioner may deploy the stent from a distal end of the delivery catheter assembly 104 through manipulation of one or more components of the handle assembly 102.

Figure 2:
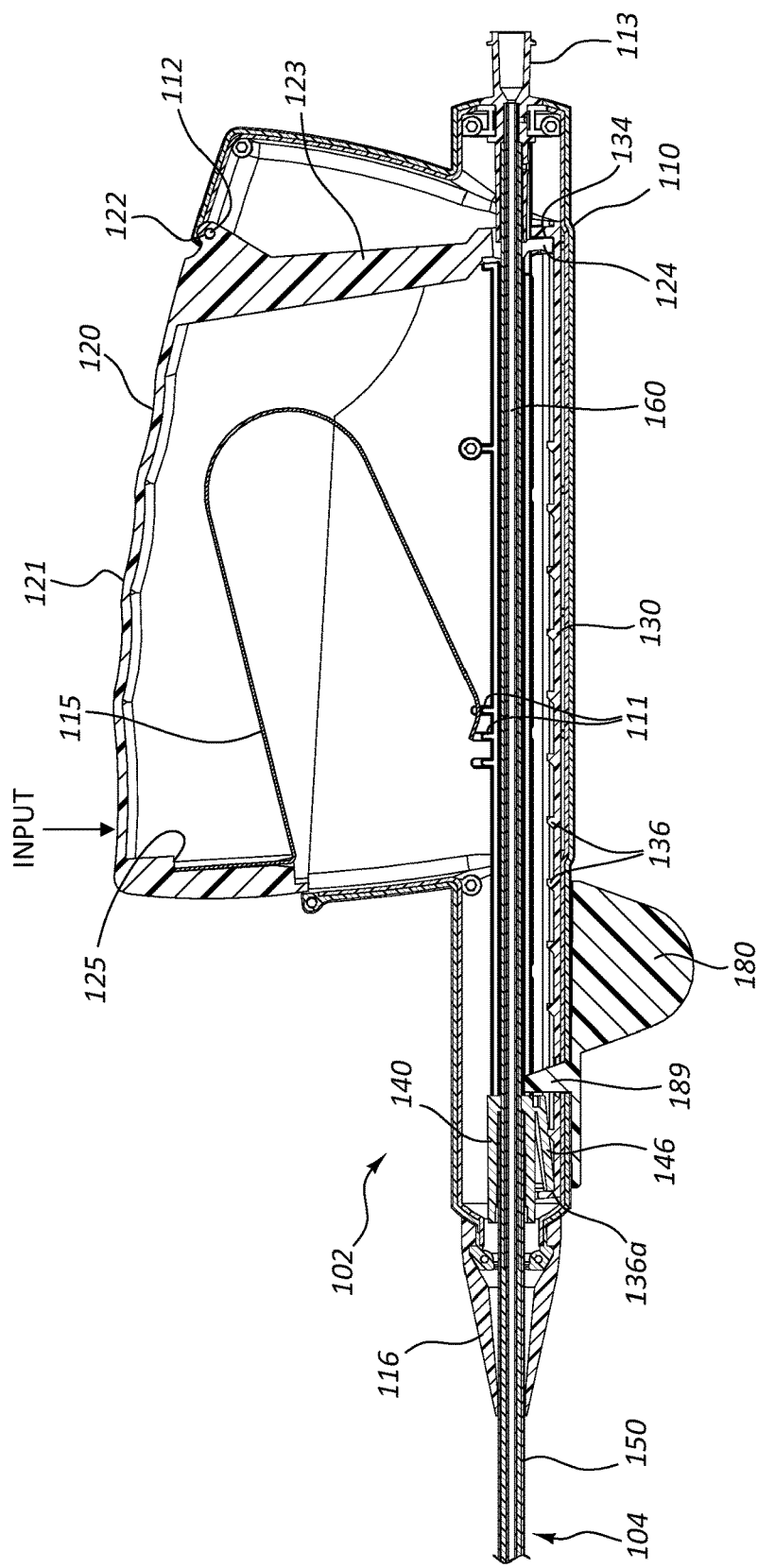
FIG. 2 is a cross-sectional view of a portion of the deployment device of FIG. 1.

FIG. 2 is a cross-sectional view of a portion of the deployment device 100 of FIG. 1. Specifically, FIG. 2 is a side view of a portion of the deployment device 100 of FIG. 1, taken through a cross-sectional plane extending vertically and intersecting a longitudinal axis of the deployment device 100, when the deployment device 100 is positioned as shown in FIG. 1. The longitudinal axis of the deployment device 100 extends along the center of the delivery catheter assembly 104, including along the center of components of the delivery catheter assembly 104 which overlap with the handle 102 assembly, such as the intermediate sheath 160, as shown in FIG. 2.

As the handle assembly 102 is configured to be grasped or otherwise manipulated by a user and the delivery catheter assembly 104 configured to extend to a treatment location within a patient's body, along the longitudinal axis, the delivery catheter assembly 104 extends in a distal direction away from the handle assembly 102. The proximal direction is opposite, correlating to a direction defined along the longitudinal axis, extending from the delivery tip 174 toward the handle assembly 104.

FIG. 2 depicts various internal components of the handle assembly 102, exposed by the cross-sectional view. A portion of the delivery catheter assembly 104 is also shown extending from the handle assembly 102. The handle assembly 102 comprises a housing 110. The housing 110 surrounds certain components of the handle assembly 102, as shown, providing a grip surface for a practitioner.

The housing 110 is operably coupled to an actuator 120. Manipulation of the actuator 120 with respect to the housing 110 may be configured to deploy the stent, as further detailed below. In the depicted embodiment, the actuator 120 is rotatably coupled to the housing 110 by a pin 112. The pin 112 extends from the housing 120 and may be integrally formed with one or more other portions of the housing 110. As shown, the pin 112 extends through a pin aperture 122 in the actuator 120.

Other arrangements for operably coupling the actuator 120 and the housing 110 are within the scope of this disclosure. For example, the pin 112 may be integral with a portion of the actuator 120 and may be received in an opening, sleeve, or aperture formed in the housing 110. Other types of designs of rotatable couplings, including a separate coupling component such as a hinge are within the scope of this disclosure. Still further, a compliant mechanism, such as deformable flange, may be utilized to rotatably couple the actuator 120 and the housing 110, including compliant couplings integrally formed with the actuator 120, the housing 110, or both. Moreover, it is within the scope of this disclosure to slidably couple an actuator (such as actuator 120) to a housing (such as housing 110). Configurations wherein the actuator 120 is manipulation through rotation, translation, or other displacement relative to the housing 110 are all within the scope of this disclosure.

The actuator 120 comprises an input portion 121 extending from the aperture 122. In the depicted embodiment, the input portion 121 comprises a surface, at least partially exposed with respect to the housing 110. In operation, a user may manipulate the actuator 120 by exerting a force on the input portion 121, illustrated by the arrow labeled "input" in FIG. 2, displacing the input portion 121 generally toward the longitudinal axis of the deployment device (100 of FIG. 1) and causing the actuator 120 to rotate about the pin 112 with respect to the housing 110. Displacement of the actuator 120 due to a force such as illustrated by the arrow labeled "input" corresponds to "depression" of the actuator 120 or "depression of the actuator 120 with respect to the housing 110."

The actuator 120 may further comprise a transfer arm 123 extending from the pin aperture 122. The transfer arm 123 may be rigidly coupled to the input portion 121, including embodiments wherein both the transfer arm 123 and the input portion 121 are integrally formed with the rest of the actuator 120. The transfer arm 123 extends to a ratchet slide engaging portion 124. Depression of the input portion 121, in the direction shown by the arrow labeled "input" displaces the transfer arm 123 as the actuator 120 is rotated about the pin 112.

Depression of the input portion 121 thus causes displacement of the ratchet slide engaging portion 124 with respect to the housing 110. This displacement of the ratchet slide engaging portion 124 can be understood as rotation about the pin 112 having a proximal translation component and a vertical translation component, as rotation of the input portion 121 in the direction indicated by the arrow labeled "input" will displace (with respect to the housing 110) the ratchet slide engaging portion 124 both proximally and vertically.

A spring 115 may be disposed between the actuator 120 and the housing 110. The spring 115 may be configured to resist displacement of the actuator 120 in the direction indicated by the arrow labeled "input" and may be configured to return the actuator to the relative position shown in FIG. 2 after it has been depressed by a user. When the handle assembly 102 is unconstrained, the spring 115 may thus maintain (or return to) the relative position of the actuator 120 with respect to the handle 110 as shown in FIG. 2.

In the illustrated embodiment, the spring 115 engages with a spring ledge 125 of the actuator 120 and spring protrusions 111 of the housing 110. The spring protrusions 111 may provide a bearing surface for the spring 115 offset from movable internal components of the handle assembly 102 (such as the carrier 140 further detailed below). Though three spring protrusions 111 are shown in the depicted embodiment, more or few protrusions, or use of other features such as ridges, ledges, shoulders, and so forth are within the scope of this disclosure.

The depicted embodiment comprises a leaf spring 115. Other biasing elements, such as coil springs, piston assemblies, compliant mechanisms, and so forth are likewise within the scope of this disclosure. In some instances, a compliant portion of one or both of the housing 110 and actuator 120 may provide a biasing force analogous to that provided by the spring 115. Leaf springs, such as spring 115, may be configured to provide a relatively constant biasing force notwithstanding compression of the spring 115 as the actuator 120 is rotated depressed with respect to the housing 110.

As the actuator 120 is depressed with respect to the housing 110, the spring 115 compresses and the ratchet slide engaging portion 124 is displaced as described above. Again, the displacement of the ratchet slide engaging portion 124 with respect to the housing 110 can be understood as having a proximal component and a vertical component.

The ratchet slide engaging portion 124 may be operably coupled to a ratchet slide 130 such that displacement of the ratchet slide engaging portion 124 likewise displaces the ratchet slide 130. The ratchet slide 130 may be constrained such that the ratchet slide 130 is configured only for proximal or distal displacement with respect to the housing 110. Thus, operable coupling of the ratchet slide engaging portion 124 to the ratchet slide 130 may allow for sliding interaction between the ratchet slide engaging portion 124 and the ratchet slide 130 such that only that proximal or distal component of the displacement of the ratchet slide engaging portion 124 is transferred to the ratchet slide 130. Stated another way, the ratchet slide 130 may be displaced in a direction parallel to the longitudinal axis of the deployment device 100 while the input displacement may be at an angle to the longitudinal axis of the deployment device 100. It is noted that, in the configuration shown in FIG. 2, the safety member 180 may prevent proximal displacement of the ratchet slide 130. The safety member 180, including removal thereof, is discussed in more detail below. Discussion herein relating to displacement of the ratchet slide 130 and related components, may thus be understood as disclosure relevant to a configuration of the handle assembly 102 in which the safety member 180 has been removed.

As the actuator 120 is depressed with respect to the housing 110, the ratchet slide 130 may thus be proximally displaced with respect to the housing 110. One or both of the ratchet slide 130 and actuator 120 may also interact with the housing 110 such that there is a positive stop to arrest the depression of the actuator 120 and/or proximal displacement of the ratchet slide 130. This positive stop may be an engaging ledge, shoulder, lug, detent, or other feature coupled to the housing 110, including features integrally formed on the housing 110.

A full stroke of the actuator 120 may thus correspond to displacement from the unconstrained position shown in FIG. 2, to the positive stop caused by interaction with the housing 110 when the actuator 120 is depressed. Release of the actuator 120 following a full or a partial stroke may then result in return of the actuator 120 to the unconstrained state, due to the biasing force provided by the spring 115. The unconstrained state shown in FIG. 2, refers to lack of constraint due to user input. In this state, the spring 115 may be partially compressed, and interaction between the actuator 120 and the housing 110 may prevent rotation of the actuator 120 about the pin 112 in the opposite direction to depression of the actuator 120, or the return direction. In other words, interaction between the actuator 120 and the housing 110 (or features of the housing 110) may create a positive stop to the return motion of the actuator 120 as well.

Referring to both FIGS. 1 and 2, the actuator 120 and the housing 110 may be coupled such that pinching of external materials (such as a practitioner's hand or a surgical drape) is minimized when the actuator 120 is depressed or returned. For instance, the actuator 120 may comprise a shell configured to mate with, and slide into, the housing 110. Though the components may slide and rotated with respect to each other, the interface of the components may be sufficiently close and/or smooth to minimize pinching or other engagement of external materials. This close and/or smooth interface may refer to interaction at the edges of the actuator 120 as it is displaced into the housing 110 and/or to interaction at the portion of the actuator 120 near the pin 112, as the actuator 120 returns to the unconstrained position.

As also shown in FIGS. 1 and 2, the input portion 121 of the actuator 120 may also comprise ridges or other features to facilitate handling or gripping of the actuator 120 during use.

Referring again to FIG. 2, the ratchet slide 130 may thus be proximally displaced during depression of the actuator 120. Again, such displacement may correspond to a configuration in which the safety member 180 shown in FIG. 2 has been removed. Proximal displacement of the ratchet slide 130 may also proximally displace the carrier 140 due to interaction between one or more carrier engaging ratchet lugs 136 on the ratchet slide 130 and a ratchet slide engaging arm 146 coupled to the carrier 140.

FIG. 3A is a perspective view of the ratchet slide 130 of the deployment device 100 of FIGS. 1 and 2. FIG. 3B is a cross-sectional view of the ratchet slide 130 of FIG. 3A, taken through a vertical plane disposed along a longitudinal centerline of the ratchet slide 130. When the ratchet slide 130 is disposed within the handle assembly 102 of FIG. 2, this cross-sectional plane would intersect the longitudinal axis of the deployment device 100.

As shown in FIGS. 2, 3A, and 3B, the ratchet slide 130 may comprise a plurality of carrier engaging ratchet lugs 136. The carrier engaging ratchet lugs 136 may be spaced at even intervals along the longitudinal direction of the ratchet slide 130. In the figures, exemplary carrier engaging ratchet lugs are denoted with reference numeral 136, while the distal most carrier engaging ratchet lug, disposed at the distal end of the ratchet slide 130 is denoted with reference numeral 136a.

The ratchet slide 130 further comprises a ratchet slide safety opening 139 and an actuator engaging opening 134. These features are discussed in more detail below.

As noted above, interaction between the ratchet slide engaging portion 124 of the actuator 120 and the ratchet slide 130 may proximally displace the ratchet slide 130 with respect to the housing 110. Engagement between the carrier 140 and one of the carrier engaging ratchet lugs 136 may also proximally displace the carrier 140 as the ratchet slide 130 is proximally displaced with respect to the housing 110.

In the configuration of FIG. 2, the ratchet slide engaging arm 146 of the carrier 140 is engaged with the distal most carrier engaging ratchet lug 136a.

FIG. 4 is a side view of the carrier 140 of the deployment device 100 of FIGS. 1 and 2. As shown in FIG. 4, the ratchet slide engaging arm 146 extends radially away from a longitudinal axis of the carrier 140. When the carrier is disposed within the handle assembly 102 of FIG. 2, the longitudinal axis of the carrier 140 is disposed along the longitudinal axis of the deployment device 100.

Figure 5:
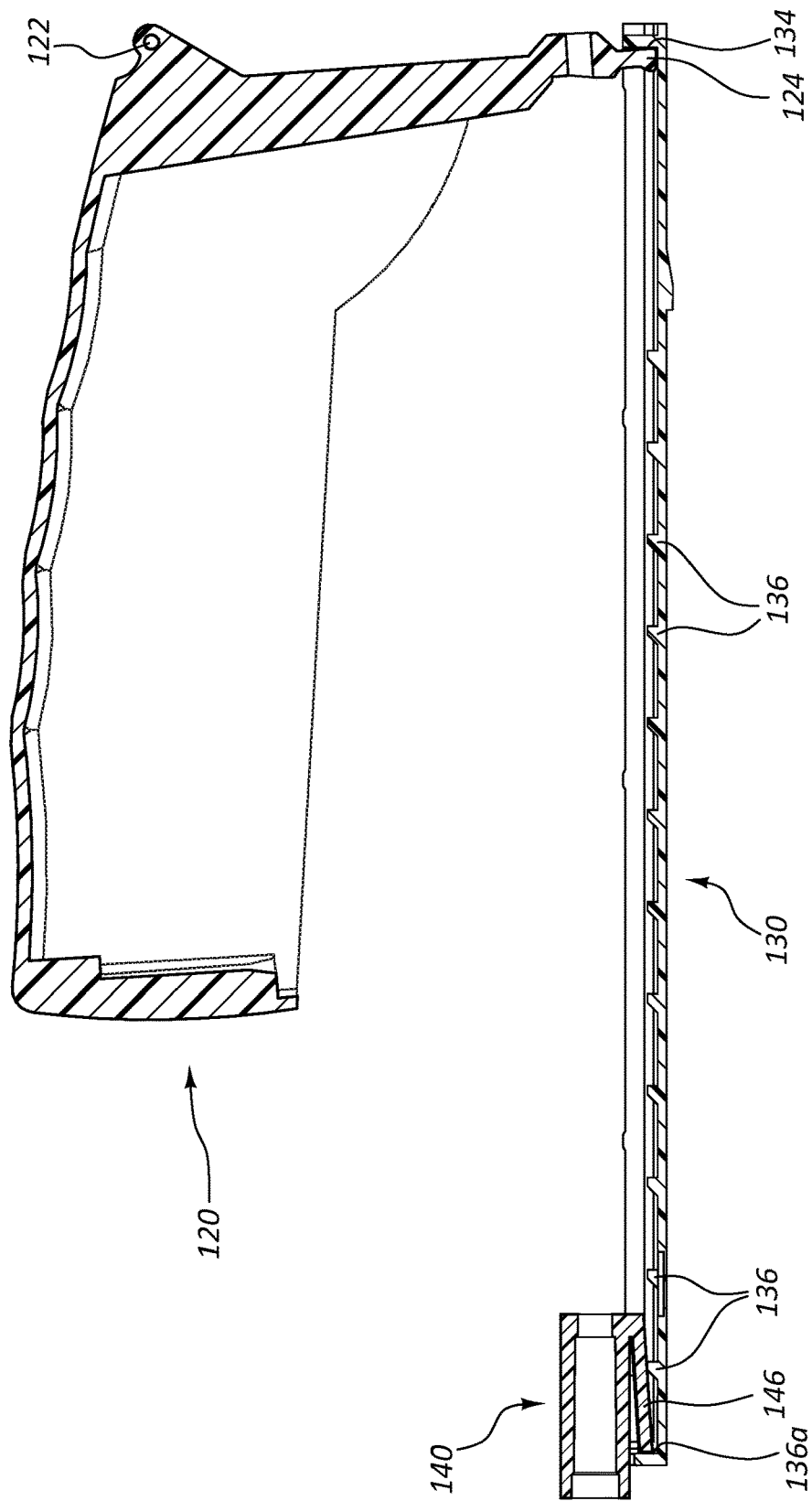
FIG. 5 is a cross-sectional view of another portion of the deployment device shown in FIGS. 1 and 2.

FIG. 5 is a cross-sectional view of a portion of the deployment device 100 shown in FIGS. 1 and 2. Specifically, the actuator 120, ratchet slide 130, and carrier 140 are shown in FIG. 5, in the same relative positions, and along the same cross-sectional plane as in FIG. 2.

Referring to FIGS. 2-5, during depression of the actuator 120 with respect to the housing 110, the actuator 120 rotates around the pin aperture 122. This rotation causes displacement of the ratchet slide engaging portion 124 of the actuator 120. The component of this displacement correlating to proximal displacement of the ratchet slide engaging portion 124 also proximally translates the ratchet slide 130 due to interaction between the ratchet slide engaging portion 124 of the actuator 120 and the actuator engaging opening 134 of the ratchet slide 130. Stated another way, the walls or faces that define the actuatory engaging opening 134 may contact the ratchet slide engaging portion 124 such that the ratchet slide 130 is displaced when the actuator 120 is displaced.

Proximal displacement of the ratchet slide 130 also proximally displaces the carrier 140 due to interaction between the carrier engaging ratchet lugs 136 and the ratchet slide engaging arm 146. In the depicted embodiment, a distal surface of the ratchet slide engaging arm 146 is in contact with a proximal face of the distal most carrier engaging ratchet lug 136a. This contact exerts proximal force on the distal surface of the ratchet slide engaging arm 146, displacing the carrier 140 in a proximal direction. Accordingly, the ratchet slide 130 and carrier 140, will move proximally until the actuator 120 reaches the end of the stroke.

Figure 6:
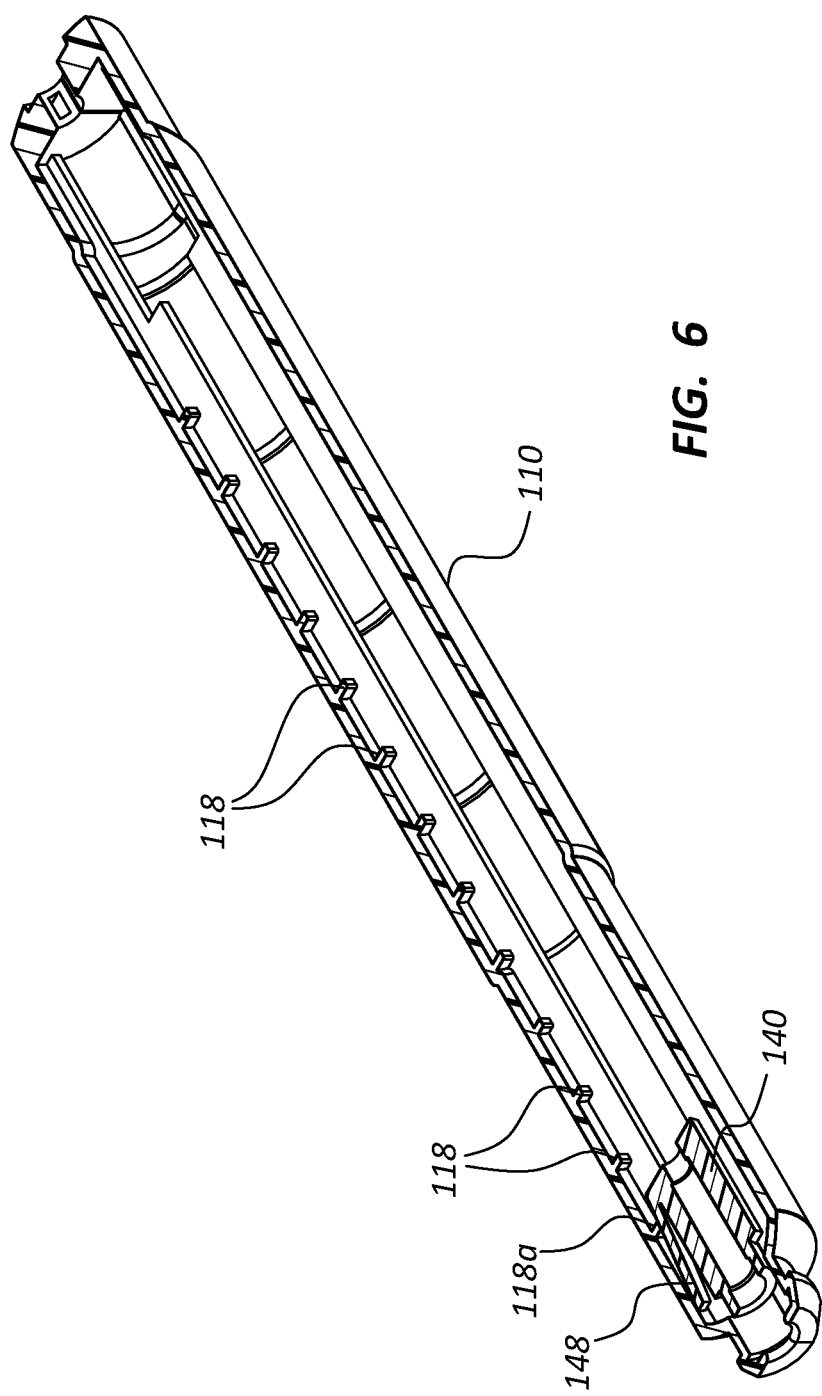
FIG. 6 is a cross-sectional view of yet another portion of the deployment device shown in FIGS. 1 and 2.

FIG. 6 is a cross-sectional view of the housing 110 and the carrier 140 in the same relative positions shown in FIG. 2. The cross-sectional plane of FIG. 6 extends along the longitudinal axis of the deployment device, however, the cross-sectional plane of FIG. 6 extends horizontally, orthogonal to the cross-sectional planes of FIGS. 2, 3B, and 5.

As shown in FIG. 6, the carrier 140 comprises a housing engaging arm 148 extending radially away from a longitudinal axis of the carrier 140. The housing 110 comprises a plurality of carrier engaging housing lugs 118. In FIG. 6, exemplary carrier engaging housing lugs are denoted by reference numeral 118, with the distal most carrier engaging housing lug denoted by reference numeral 118a.

Referring to FIGS. 2-6, as interaction between the actuator 120, ratchet slide 130, and carrier 140 displaces the carrier 140 with respect to the housing 110 (as shown and described above), the housing engaging arm 148 (shown in FIG. 6) of the carrier 140 will deflect radially inward due to contact with one of the carrier engaging housing lugs 118. For example, from the position shown in FIG. 6, as interaction between the distal most carrier engaging ratchet lug 136a and the ratchet slide engaging arm 146 of the carrier 140 draws the carrier 140 proximally, the distal most carrier engaging housing lug 118a causes the housing engaging arm 148 to displace radially inward. The housing engaging arm 148 will continue to deflect radially inward until the distal end of the housing engaging arm 148 is positioned proximal of the distal most carrier engaging housing lug 118a, at which point the housing engaging arm 148 will return to the radially outward configuration shown in FIG. 6. The point at which the housing engaging arm 148 moves proximally of the distal most carrier engaging housing lug 118a, may correspond to the stroke of the actuator 120, such that engagement between the housing engaging arm 148 and the next carrier engaging housing lug 118 (moving in a proximal direction) occurs at the end of the stroke, which may correspond to contact between the ratchet slide 130 and/or actuator 120 and a positive stop on the housing 110 defining the end of the stroke.

As the actuator 120 is released following the stroke, interaction between the spring 115, the housing 110, and the actuator 120 will return the actuator 120 to the unconstrained position (the position shown in FIG. 2) as discussed above. Corresponding rotation of the actuator 120 about the pin aperture 122 will thus correlate to displacement of the ratchet slide engaging portion 124, including a component of displacement in the distal direction. Interaction between the ratchet slide engaging portion 124 and the actuator engaging opening 134 will then correlate to distal displacement of the ratchet slide 130. Thus, when the actuator 120 is released at the end of a stroke, the actuator 120, the spring 115, and the ratchet slide 130 return to the same positions relative to the housing as shown in FIG. 2.

As the actuator 120 returns to the unconstrained position, however, interaction between the housing engaging arm 148 and the carrier engaging housing lug 118 prevents distal displacement of the carrier 140. Specifically, the distal surface of the housing engaging arm 148 will be in contact with a proximal facing surface of a carrier engaging housing lug 118, the interaction preventing the carrier 140 from returning to the pre-stroke position. In the exemplary stroke discussed above, the distal most carrier engaging housing lug 118a displaced the housing engaging arm 148 during the stroke, and the housing engaging arm 148 engaged with the distal most carrier engaging housing lug 118a following the stroke. Subsequent strokes move the carrier 140 along the plurality of carrier engaging housing lugs 118 in a proximal direction.

As the actuator 120 returns to the unconstrained state, radially inward displacement of the ratchet slide engaging arm 146 of the carrier 140 allows the ratchet slide 130 to move distally with respect to the carrier 140, as engagement between the carrier 140 and the carrier engaging housing lugs 118 arrest distal displacement of the carrier 140.

Referring to FIGS. 2-6, with particular reference to the view of FIG. 5, distal displacement of the ratchet slide 130 with respect to the carrier 140, creates interaction between the carrier engaging ratchet lugs 136 and the ratchet slide engaging arm 146 causing the ratchet slide engaging arm 146 to displace radially inward. The proximal facing surface of the carrier engaging ratchet lugs 136 may be angled to facilitate this interaction. In the exemplary stroke discussed above, engagement between the distal most carrier engaging ratchet lug 136a displaced the carrier 140 in a proximal direction; during the return of the actuator 120, the next carrier engaging ratchet lug 136 (in a proximal direction) causes the radially inward displacement of the ratchet slide engaging arm 136 until the ratchet slide engaging arm 136 is proximal of the carrier engaging ratchet lug 136. At that point the ratchet slide engaging arm 136 returns to a radially outward position (analogous to that shown in FIG. 5) though the distal surface of the ratchet slide engaging arm 136 is now engaged with a proximal face of the next carrier engaging ratchet lug 136 (again in a proximal direction).

Displacement of the ratchet slide 130 sufficient to move to engagement with a subsequent carrier engaging ratchet lug 136 may correspond with the magnitude of ratchet slide 130 displacement corresponding to a return of the actuator 120. Subsequent returns of the actuator 120 following strokes move the ratchet slide 130 such that the plurality of carrier engaging ratchet lugs 136 may serially engage the carrier 140, stroke after stroke.

Accordingly, as described above, depressing the actuator 120 for a full stroke, then allowing the actuator 120 to return to the unconstrained position, displaces the carrier 140 with respect to the housing 110 in discrete increments, corresponding to the distance between adjacent carrier engaging housing lugs 118 along the longitudinal direction. Interaction of the actuator 120, positive stops associated with the housing 110, carrier arms 134, 136, and lugs 118, 136 may also combine to give a user tactile and audible feedback as the carrier 140 is incrementally displaced. Further, one or more opening in the housing 110 may allow a user to observe the relative position of the carrier 140 providing further feedback as to carrier 140 position.

As detailed below, the relative position of the carrier 140 with respect to the housing 110 may correlate to the degree of deployment of a stent from the deployment device 100. Thus, visual, audible, and tactile feedback as to the position of the carrier 140 provides a user with information regarding stent deployment during use of the deployment device 100. This information may correlated to increased control during deployment as the practitioner quickly and intuitively can surmise the degree of stent deployment.

As outlined above, tactile and/or audible feedback back result from the interactions of the carrier 140, ratchet slide 130, housing 110, and/or actuator 120. For example, as the ratchet slide engaging arm 146 or housing engaging arm 148 of the carrier 140 deflect radially inward then return outward, there may be an audible and/or tactile response.

The device may be configured for visual feedback of relating to the relative deployment of a stent. For example, in some embodiments, the housing 110 may comprise viewing windows to allow a practitioner to observe the position of the carrier 140 relative to the housing 110. Further, indicia on the housing 110 may correlate the position of the carrier 140 to the degree of deployment of a stent.

The increments of displacement of the carrier 140 may correlate to standard stent lengths or units of measure. For example, many stents are sized in 1 cm increments. Configuration of the increments of displacement on the carrier 140 in 1 cm increments would thus directly correlate with stent length at a 1:1 ratio. Any other ratio, including embodiment wherein a stroke correlates to a greater length (such as 2, 3, 4, or 5 cm) or a lesser length (such as 0.25, 0.5, or 0.75 cm) are likewise within the scope of this disclosure.

The deployment device 100 may be configured as a universal device operable with various stent lengths. In some embodiments a practitioner may directly equate the number of strokes needed to deploy a stent with the length of the stent loaded in the deployment device 100 (such as four strokes for a four centimeter stent). Further, a single design of deployment device 100 may be utilized with various lengths of stents, with a maximum length related to the maximum length of travel of the carrier 140.

The nature of depression of the actuator 120 may facilitate one handed operation and may be ergonomically designed. First, a practitioner need only grip the deployment device with one hand to depress the actuator, leaving a second hand free for other therapy needs. Further, the direction with which the deployment device is gripped, with the practitioner's hand extending laterally away from the longitudinal axis of the deployment device and the lateral direction of depression, as opposed, for example to longitudinal gripping to actuate, may be ergonomically desirable. Lateral gripping and input may more readily present the deployment device 100 for use when the delivery catheter assembly 104 is disposed within a patient's body, not requiring the practitioner to move to an awkward stance with respect to other therapy tools. Further, the input portion 121 of the actuator 120 may provided additional surface for a practitioner to grip, facilitating use of a greater portion of a practitioner's hand for actuation, as compared to a finger trigger or similar actuation mechanism.

The incremental displacement of the carrier 140 may further facilitate partial deployment of a stent, allowing a practitioner to deploy the stent in increments, potential adjusting or confirming the position of the stent between these increments.

Still further, the deployment device 100 may be configured for use with either the right or left hand, or gripped with the fingers or palm in contact with the actuator 120 without changing the design of the deployment device 100. These features may further increase user comfort and control. Viewing windows in the housing 110 to confirm the position on the carrier 140 may be located on one or both sides of the housing 110 and may be associated with indicia correlating to stent length or other factors.

Moreover, the relative lengths of the input portion 121 and transfer arm 123 of the actuator 120 may be configured to provide mechanical advantage when deploying a stent. This may increase comfort and control during use. The ratio of the length of the input portion 121—from its distal end to the pin aperture 122—to the length of the transfer arm 123—from the pin aperture 122 to the ratchet slide engaging portion 124—may be greater than or equal to 1.5:1, including 2:1, 2.5:1, 3:1, 3.5:1 or greater. This ratio correlates to the mechanical advantage provided by the device. In some instances the mechanical advantage provided may be 1.5:1, 2:1, 2.5:1, 3:1, 3.5:1 or greater. Stated another way, the ratio of length of travel of the input portion 121 to the corresponding length of travel of the ratchet slide engaging portion 124 may be 1.5:1, 2:1, 2.5:1, 3:1, 3.5:1 or greater. Accordingly, the input force applied against the input portion 121 may result in a greater force exerted by the ratchet slide engaging portion 124 on the ratchet slide 130. The ratio of the force exerted on the ratchet slide 130 to the input force may be 1.5:1, 2:1, 2.5:1, 3:1, 3.5:1 or greater.

Figure 7:
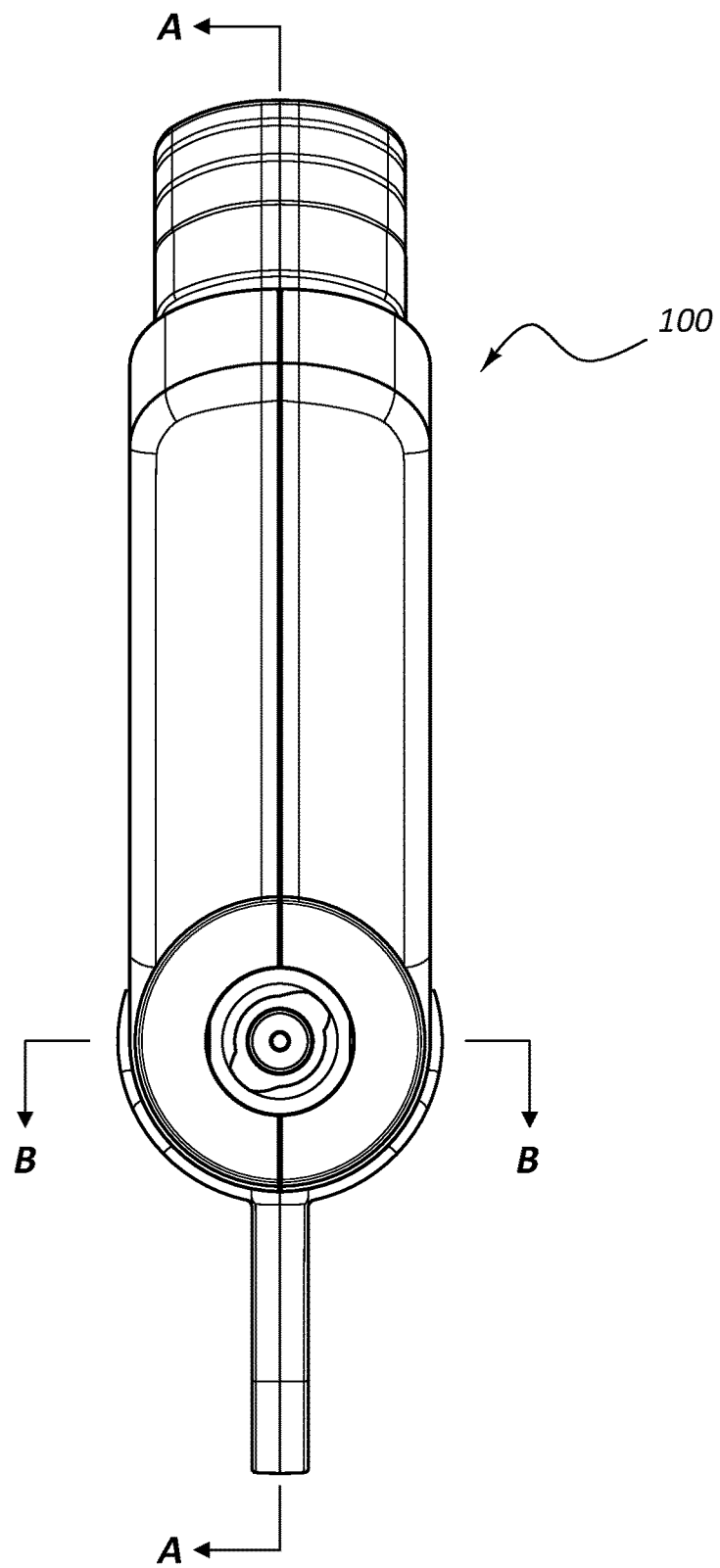
FIG. 7 is a front view of the deployment device of FIG. 1, illustrating certain cross-sectional planes described herein.

FIG. 7 is a front view of the deployment device 100, illustrating two cross-sectional planes. Specifically, plane A-A extends vertically along the longitudinal axis of the deployment device 100 viewing the exposed components in a right to left direction. Plane A-A corresponds to the cross-sectional plane of FIGS. 2, 3B, and 5. Plane B-B also extends from the longitudinal axis of the deployment device 100, though Plane B-B extends horizontally therefrom. Plane B-B corresponds to the cross-sectional plane of FIG. 6, and is viewed from a top to bottom direction. The longitudinal axis of the deployment device 100 is in both planes A-A and B-B, with the line defined as the intersection between these planes being the same line as the longitudinal axis as referenced herein.

Figure 8:
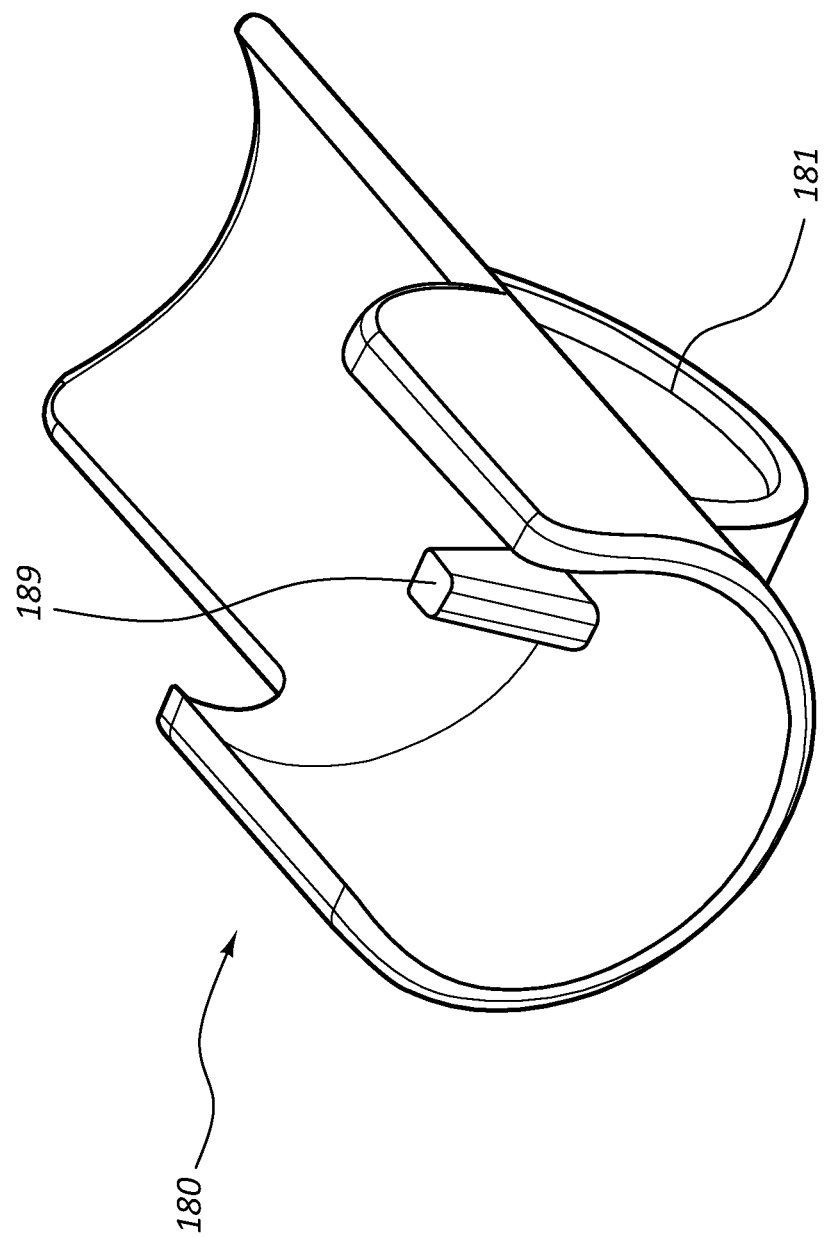
FIG. 8 is a perspective view of the safety member of the deployment device of FIG. 1.

Additionally, as stated above, the deployment device 100 may comprise a safety member 180. FIG. 8 is a perspective view of the safety member 180 of the deployment device 100. The safety member 180 may be configured with a circular or partially circular opening configured to snap onto an outside surface of a portion of the deployment device 100. Referring to both FIG. 2 and FIG. 8, the safety member 180 may comprise a safety lug 189 that extends through a ratchet slide safety opening (139 of FIG. 3A) and a similar safety opening in the housing 110 (not shown). When the safety lug 189 is disposed within these openings, the safety lug 189 may prevent proximal displacement of the carrier 140 and the ratchet slide 130, thus preventing inadvertent deployment of a stent. A practitioner may leave the safety member 180 in place during displacement of the delivery catheter assembly 104 to a treatment region. Due to interactions between the carrier 140, ratchet slide 130, and actuator 120, the safety member 180 likewise prevents displacement of the actuator 120 when the safety lug 189 extends through the openings.

In the depicted embodiment, the safety lug 189 extends through a bottom portion of the housing 110 and ratchet slide 130. In other embodiments, the safety lug 189 may extend through a top surface of the housing 110, interacting with the carrier 140 but not directly with the ratchet slide 130. Nevertheless, prevention of proximal displacement on the carrier 140 only, will also prevent displacement of the ratchet slide 130 and the actuator 120 due to the interaction between these elements.

In some embodiments, the safety member 180 may be tethered to the deployment device 100, or may comprise a sliding switch or other element operably coupled to the housing 110 or other components of the deployment device 100. In the depicted embodiment, the safety member 180 is removably coupled.

Figure 9:
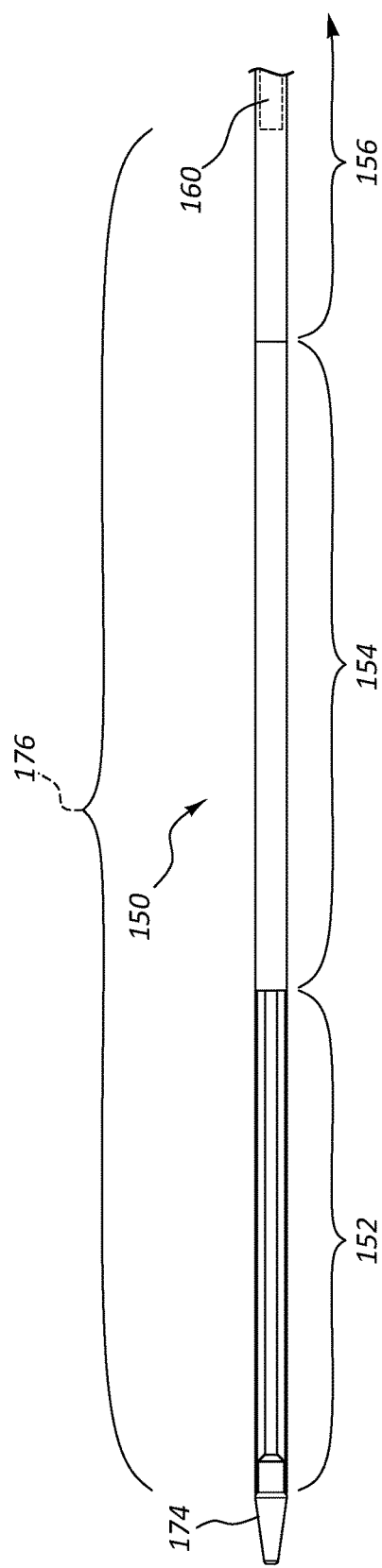
FIG. 9 is a side view of a portion of the delivery catheter assembly of the deployment device of FIG. 1.
Figure 10:
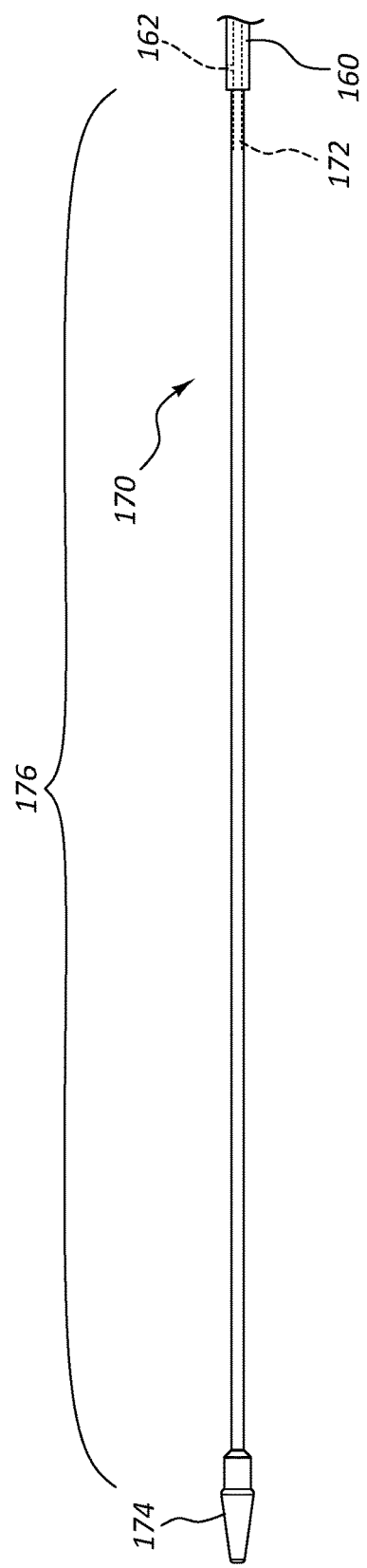
FIG. 10 is a side view of another portion of the delivery catheter assembly of the deployment device of FIG. 1.

FIG. 9 is a side view of a portion of the delivery catheter assembly 104 of the deployment device 100. Specifically, FIG. 9 is a side view of a distal section of the delivery catheter assembly 104. FIG. 10 is a side view of the same longitudinal section of the delivery catheter assembly 104 as shown in FIG. 9, however, the outer sheath (150 of FIG. 9) has been removed to show other components.

Referring to FIGS. 1, 2, 9, and 10, the delivery catheter assembly 104 may be configured to deploy a stent as the deployment device 100 is manipulated, as discussed above. The delivery catheter assembly 104 may comprise an outer sheath 150, extending from the handle assembly 102. The outer sheath 150 may be fixedly coupled to the carrier 140. The delivery catheter assembly 104 may further comprise an intermediate sheath 160 and an inner sheath 170, both disposed within the outer sheath 150, and both fixedly coupled to the housing 110. Thus, proximal displacement of the carrier 140 with respect to the housing 110, will proximally displace the outer sheath 150 with respect to both the intermediate sheath 160 and the inner sheath 170.

The outer sheath 150 may comprise a shaft section 156 extending from the carrier 140 in a distal direction. At the distal end of the shaft section 156 the outer sheath 150 may comprise a flex zone 154 extending from the shaft section 156 in a distal direction. Finally, the outer sheath 150 may comprise a pod 152 extending from the flex zone 154 in a distal direction. (As shown in FIG. 9, the pod 152 may be transparent.)

The shaft section 156 of the outer sheath 150 may have a different stiffness and/or durometer than the flex zone 154 and/or the pod 152. The flexibility toward the distal end of the outer sheath 150 may improve trackability of the delivery catheter assembly 104 over a guidewire and may be less traumatic, while a stiffer shaft may be more kink resistant and/or transmit displacement and/or torque along the shaft section 156.

The pod 152 may be configured to retain a crimped or otherwise constrained stent. Removal of the pod 152 from the stent may allow the stent to self-expand, and thereby deploy. It is within the scope of this disclosure for the pod 152 to be any relative length, the flex zone 154 to be any relative length, and the shaft section 156 to be any relative length. Thus, in some instances, a constrained stent may be in one, two, or all three of these portions of the outer sheath 150. For example, in the illustrated embodiment, an annular space 176 (described further below), configured to receive a crimped stent extend along the pod 152 as well as portions of the flex zone 154 and shaft section 156. In other embodiments, the annular space 176 may correlate just to the pod 152 segment, meaning the device is configured to retain a crimped stent only within the pod 152 segment.

The distal tip 174 of the delivery sheath assembly 104 may be coupled to and/or integrally formed with the inner sheath 170. A lumen 172 may extend along the inner sheath 170 from the proximal end of the deployment device 100 to the distal tip 174. A luer fitting 113 coupled to the housing 110 may be in communication with the lumen 172. A guidewire may thus extend through the luer fitting 113 through the lumen 172 and out of the distal tip 174. Further, fluid introduced into the luer fitting 113 may be utilized to flush the lumen 172.

The inner sheath 170 may be fixed to the housing, for example, at the proximal end of the inner sheath 170. An intermediate sheath 160, also fixed to the housing 110, may extend over a portion of the inner sheath 170. The intermediate sheath 160 and inner sheath 170 may or may not be directly fixed to each other. In some embodiments, the intermediate sheath 160 may be a close slip fit over the inner sheath 170.

The inner sheath 170 extends distally beyond a distal end of the intermediate sheath 160, creating an annular space 176 between the inner sheath 170 and the outer sheath 150 adjacent the distal tip 174, extending proximally to the distal end of the intermediate sheath 160. This annular space 176 may be configured to retain a crimped stent.

As the deployment device 100 is manipulated to incrementally displace the carrier 140 with respect to the housing 110, the outer sheath 150 is incrementally displaced proximally with respect to the inner sheath 170 and intermediate sheath 160. The distal end of the intermediate sheath 160 interacts with the proximal end of the stent, preventing the stent from being drawn back with the outer sheath 150. Thus, the stent is incrementally exposed, and allowed to self-expand and deploy.

In some embodiments, a fluid aperture 162 in the intermediate sheath 160 may extend through the wall of the intermediate sheath 160 and the wall of the inner sheath 170, into fluid communication with the inner lumen 172. This fluid aperture 162 may thus provide fluid communication between the annular space 176 and the inner lumen 172, as fluid within the inner lumen 172 can move through the fluid aperture 162 and into the annular space 176. This communication may be used to flush the annular space 176, during use, which may be configured to remove air or other unwanted materials in the annular space 176 or around the crimped stent.

The distal tip 174 may comprise a flexible material and may be configured to be atraumatic. The distal tip 174 may comprise nylons including PBAX.

In some instances braided or coil reinforcements may be added to the outer sheath 150, the intermediate sheath 160, and/or the inner sheath 170 to increase kink resistance and/or elongation. Reinforcing members may comprise stainless steel, nitinol, or other materials and may be round, flat, rectangular in cross section, and so forth.

One, two, or all of the outer sheath 150, the intermediate sheath 160, and/or the inner sheath 170 may be configured with varying durometers or other properties along the length thereof. In some instances the outer sheath 150 may be configured with a proximal section with a durometer between 72 and 100 on the Shore D scale or may be greater than 100 on the Shore D scale. A second portion of the outer sheath 150 may comprise a durometer of 63 on the Shore D scale, and a distal section with a durometer between 40 and 55 on the Shore D scale. Any of these values, or the limits of any of the ranges may vary by 15 units in either direction. In some instances the second portion will begin about 6 inches from the distal end of the outer sheath 150 and the distal section will begin about three inches from the distal end of the outer sheath 150. These sections may or may not correspond to the shaft section 156, the flex zone 154, and the pod 152 as described above. The intermediate sheath 160 may be configured with varying durometer zones within the same ranges of hardness and length.

Any of the inner sheath 170, intermediate sheath 160, and outer sheath 150 may have differing durometer or flex zones along their lengths, and these zones may overlap in various ways to create various stress/strain profiles for the overall delivery catheter assembly 104. Overlapping of such zones may reduce tendency to kink, including tendency to kink at transition zones. Further the housing 110 may be coupled to a strain relief member 116 (as shown in FIG. 2).

Any of outer sheath 150, the intermediate sheath 160, and the inner sheath 170 may be comprised of nylons, including PBAX. Further, during manufacture, any of these members may be configured with a low friction outer surface, including through "frosting" the materials, or blowing air across the material during extrusion.

In some instances, during manufacture the distal tip 174 may be pulled into interference with the outer sheath 150, prestressing the inner sheath 170 in tension. This may reduce any effects of material creep or elongation during sterilization, keeping the distal tip 174 snugly nested with the outer sheath 150. Further, during manufacture, the interface zone between the outer sheath 150 and the carrier 140 may be configured with a tolerance zone, meaning the outer sheath 150 can be coupled to the carrier 140 at multiple points along an inside diameter of the carrier 140. This tolerance may enable manufacturing discrepancies or variations to be taken up during assembly to ensure a snug nest between the distal tip 174 and the outer sheath 150. The same tolerance fit may be applied to the inner sheath 170 and/or the intermediate sheath 160 wherein these members couple to the housing 110, including a fit zone along an inside diameter of the luer fitting 113.

In some instances, the outer sheath 150 may include indicia correlating to the degree to which a stent has been deployed. These indicia may correspond to the position of the outer sheath 150 with respect to the housing 110, as the outer sheath 150 is drawn into the housing 110, different indicia are exposed and/or covered, for example.

Further, in some instances, the deployment device 100 may be configured such that the outer sheath 150 may be distally displaced after the stent is deployed to nest the distal tip 174 in the outer sheath 150 during withdrawal of the deployment device 100 from a patient. Such configurations may include features of the handle assembly 102 that disengage the carrier 140 from one or more elements after stent deployment.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A prosthesis deployment device comprising:
an elongate delivery catheter assembly configured to retain and deploy a prosthesis;
a housing operably coupled to the delivery catheter; and
an actuator operably coupled to the housing such that displacement of the actuator displaces a portion of the delivery catheter assembly to deploy the prosthesis,
wherein the displacement of the delivery catheter assembly to deploy the prosthesis is in a direction parallel to a longitudinal axis of the deployment device and the displacement of the actuator to displace the portion of the delivery catheter assembly is in a direction disposed at an angle to the longitudinal axis of the deployment device,
wherein an arm of the actuator is coupled to a ratchet slide such that rotation of the actuator and the arm about a pin causes the arm to displace the ratchet slide parallel to the longitudinal axis of the deployment device,
wherein the actuator extends from the pin in a first direction and the arm extends from the pin in a second direction,
wherein displacement of the ratchet slide incrementally advances a carrier along the ratchet slide, and
wherein the carrier comprises a ratchet slide engaging arm that extends from the carrier to engage the ratchet slide and a housing engaging arm that extends from the carrier to engage the housing.

2. The prosthesis deployment device of claim 1, wherein the delivery catheter assembly comprises an outer sheath and the outer sheath is fixedly coupled to the carrier.

3. The prosthesis deployment device of claim 2, wherein the delivery catheter assembly comprises an inner sheath fixedly coupled to the housing.

4. The prosthesis deployment device of claim 1, wherein the deployment device provides a mechanical advantage such that an output force transferred to the portion of the delivery catheter to deploy the prosthesis is greater than an input force to displace the actuator.

5. The prosthesis deployment device of claim 4, wherein the ratio of the output force to the input force is 2:1.

6. The prosthesis deployment device of claim 1, wherein the actuator incrementally deploys the prosthesis.

7. The prosthesis deployment device of claim 5, wherein the actuator is configured to be displaceable along a stroke, and wherein one stroke of the actuator deploys only a portion of the prosthesis.

8. The prosthesis deployment device of claim 7, wherein the deployment device provides audible feedback at the end of a stroke.

9. The prosthesis deployment device of claim 7, wherein the deployment device provides tactile feedback at the end of a stroke.

10. A prosthesis deployment device comprising:
an elongate delivery catheter assembly configured to retain and deploy a prosthesis;
a housing operably coupled to the delivery catheter; and
an actuator operably coupled to the housing such that displacement of the actuator displaces a portion of the delivery catheter assembly to deploy the prosthesis, wherein the deployment device provides a mechanical advantage such that an output force transferred to the portion of the delivery catheter to deploy the prosthesis is greater than an input force to displace the actuator, wherein a stroke of the actuator displaces a portion of the delivery catheter a discrete increment and deflects an engagement arm radially inward, and the deployment device provides audible feedback when the delivery catheter is displaced the discrete increment and the engagement arm returns to its position before the stroke, and wherein the actuator is configured to rotate toward a longitudinal axis of the deployment device when displaced.

11. The prosthesis deployment device of claim 10, wherein the ratio of the output force to the input force is 2:1.

12. The prosthesis deployment device of claim 10, wherein the stroke of the actuator deploys only a portion of the prosthesis.

13. A prosthesis deployment device comprising:
an elongate delivery catheter assembly configured to retain and deploy a prosthesis;
a housing operably coupled to the delivery catheter; and
an actuator operably coupled to the housing such that displacement of the actuator displaces a ratchet slide to deploy the prosthesis,
wherein the actuator is displaceable along a stroke to deploy a portion of the prosthesis,
wherein displacement of the ratchet slide incrementally advances a carrier along the ratchet slide, and
wherein the carrier comprises a ratchet slide engaging arm that extends from the carrier to engage the ratchet slide and a housing engaging arm that extends from the carrier to engage the housing.

14. The prosthesis deployment device of claim 13, wherein the deployment device provides a mechanical advantage such that the force transferred to the portion of the delivery catheter to deploy the prosthesis is greater than an input force to displace the actuator.

15. The prosthesis deployment device of claim 14, wherein the ratio of the output force to the input force is 2:1.

16. A method of deploying a prosthesis disposed within a delivery catheter, the method comprising:
obtaining a deployment device comprising an actuator operable coupled to a delivery catheter, wherein the actuator comprises an arm coupled to a ratchet slide such that rotation of the actuator and the arm about a pin causes the arm to displace the ratchet slide parallel to the longitudinal axis of the deployment device, and wherein the actuator extends from the pin in a first direction and the arm extends from the pin in a second direction; and
displacing the actuator in a first lateral direction, wherein displacement of the actuator in the first lateral direction displaces an outer sheath of the delivery catheter in a second longitudinal direction,
wherein the actuator is configured to rotate toward a longitudinal axis of the deployment device when displaced, and
wherein actuation of the actuator displaces the outer sheath of the delivery catheter such that a portion of the prosthesis is deployed.

17. The method of claim 16, further comprising adjusting the position of the partially deployed prosthesis after displacing the actuator along a stroke.

18. A method of deploying a prosthesis disposed within a delivery catheter, the method comprising:
obtaining a deployment device comprising an actuator operable coupled to a delivery catheter; and
displacing the actuator with a first input force the deployment device configured to transfer the first input force from the actuator to a portion of the delivery catheter such that an output force exerted on the portion of the delivery catheter is greater than the first input force,
wherein the actuator is configured to rotate toward a longitudinal axis of the deployment device when displaced, and
wherein a stroke of the actuator displaces a portion of the delivery catheter a discrete increment and deflects an engagement arm radially inward, and the deployment device provides audible feedback when the delivery catheter is displaced the discrete increment and the engagement arm returns to its position before the stroke.

* * * * *